United States Patent
Wiese et al.

(10) Patent No.: US 10,092,228 B2
(45) Date of Patent: Oct. 9, 2018

(54) TISSUE OXYGEN SATURATION DETECTION AND RELATED APPARATUS AND METHODS

(71) Applicant: Dynometrics Inc., Cambridge, MA (US)

(72) Inventors: Daniel Wiese, Cambridge, MA (US); Alessandro Babini, Cambridge, MA (US); Sebastian Trousil, Boston, MA (US); Samuel Huberman, Somerville, MA (US); Stefan Kalchmair, Boston, MA (US); Pamela G. Anderson, Boston, MA (US)

(73) Assignee: Dynometrics Inc., Cambridge, MA (US)

( * ) Notice: Subject to any disclaimer, the term of this patent is extended or adjusted under 35 U.S.C. 154(b) by 0 days.

(21) Appl. No.: 15/971,870

(22) Filed: May 4, 2018

(65) Prior Publication Data

US 2018/0249937 A1    Sep. 6, 2018

Related U.S. Application Data

(63) Continuation of application No. PCT/US2017/020348, filed on Mar. 2, 2017.
(Continued)

(51) Int. Cl.
*A61B 5/1455* (2006.01)
*A61B 5/00* (2006.01)
(Continued)

(52) U.S. Cl.
CPC ........ *A61B 5/14552* (2013.01); *A61B 5/6831* (2013.01); *G06F 1/163* (2013.01); *G16H 50/20* (2018.01); *A61B 2562/043* (2013.01)

(58) Field of Classification Search
CPC ....... A61B 5/1455; A61B 5/00; A61B 5/0024; A61B 5/0095; A61B 5/14; A61B 5/145; A61B 5/1477
See application file for complete search history.

(56) References Cited

U.S. PATENT DOCUMENTS

| | | | |
|---|---|---|---|
| 6,587,703 B2 | 7/2003 | Cheng et al. | |
| 6,678,541 B1 * | 1/2004 | Durkin | G01N 21/474 600/309 |

(Continued)

FOREIGN PATENT DOCUMENTS

WO    WO 2013/023071 A1    2/2013

OTHER PUBLICATIONS

International Search Report and Written Opinion dated May 16, 2017 in connection with International Application No. PCT/US2017/020348.

(Continued)

*Primary Examiner* — Eric Winakur
(74) *Attorney, Agent, or Firm* — Wolf, Greenfield & Sacks, P.C.

(57) ABSTRACT

A wearable optical device is described for optically detecting parameters of interest within muscle, such as during physical activity or when at rest. The parameters of interest include oxygenation level and/or hemoglobin concentrations in some situations. The detected parameters, such as oxygenation level, may be used to assess physical performance, such as the extent to which the muscle is utilizing aerobic or anaerobic processes. Methods for determining the parameters of interest, such as oxygenation level, from the detected optical signals are also described, and feedback may be provided to a user.

16 Claims, 16 Drawing Sheets

Related U.S. Application Data

(60) Provisional application No. 62/409,314, filed on Oct. 17, 2016, provisional application No. 62/303,319, filed on Mar. 3, 2016.

(51) Int. Cl.
*G06F 1/16* (2006.01)
*G16H 50/20* (2018.01)

(56) References Cited

U.S. PATENT DOCUMENTS

| | | |
|---|---|---|
| 7,047,056 B2 | 5/2006 | Hannula et al. |
| 7,460,897 B1 | 12/2008 | Flessland et al. |
| 7,532,919 B2 | 5/2009 | Soyemi et al. |
| 8,668,187 B2 | 4/2014 | DelloStritto et al. |
| 8,929,967 B2 | 1/2015 | Mao et al. |
| 8,941,830 B2 | 1/2015 | Schmitz |
| 8,996,088 B2 | 3/2015 | Dasco et al. |
| 9,095,291 B2 | 8/2015 | Soller et al. |
| 9,591,999 B2 * | 3/2017 | Schenkman ......... A61B 5/1455 |
| 2008/0097173 A1 | 4/2008 | Soyemi et al. |
| 2008/0269644 A1 | 10/2008 | Ray |
| 2009/0105555 A1 | 4/2009 | Dasco et al. |
| 2011/0205535 A1 | 8/2011 | Soller et al. |
| 2012/0053431 A1 | 3/2012 | Mannheimer et al. |
| 2013/0096403 A1 | 4/2013 | Dasco et al. |
| 2015/0148624 A1 | 5/2015 | Benaron |
| 2015/0196238 A1 | 7/2015 | Dasco et al. |
| 2015/0201853 A1 | 7/2015 | Hong et al. |
| 2015/0335284 A1 | 11/2015 | Nuovo et al. |

OTHER PUBLICATIONS

International Preliminary Report on Patentability dated Mar. 30, 2018 in connection with International Application No. PCT/US2017/020348.

* cited by examiner ically in a linear arrangement along a second direction approximately perpendicular to the first direction. Methods of assessing hemoglobin concentration based on signals detected by the optical device are also provided.

TISSUE OXYGEN SATURATION DETECTION AND RELATED APPARATUS AND METHODS

CROSS-REFERENCE TO RELATED APPLICATIONS

The present application is a continuation of International Patent Application Serial No. PCT/US2017/020348, filed Mar. 2, 2017, and entitled "Tissue Oxygen Saturation Detection and Related Apparatus and Methods," which is hereby incorporated herein by reference in its entirety.

PCT Serial No. PCT/US2017/020348 is a non-provisional application claiming the benefit under 35 U.S.C. § 119(e) of U.S. Provisional Patent Application Ser. No. 62/303,319, filed Mar. 3, 2016 and entitled "Tissue Oxygenation Detection and Related Apparatus and Methods," which is hereby incorporated herein by reference in their entirety.

PCT Serial No. PCT/US2017/020348 is also a non-provisional application claiming the benefit under 35 U.S.C. § 119(e) of U.S. Provisional Patent Application Ser. No. 62/409,314, filed Oct. 17, 2016 and entitled "Tissue Oxygen Saturation Detection and Related Apparatus and Methods," which is hereby incorporated herein by reference in its entirety.

BACKGROUND

Field

The present application relates to monitoring of muscle oxygen saturation and related physical performance, as well as to related apparatus and methods.

Related Art

Oxygen is required for cells to produce energy in a process called oxidative phosphorylation. Hemoglobin is the protein in red blood cells that binds oxygen molecules for transport from the lungs to all tissues and exists in two states, oxygenated and deoxygenated. Oxygen saturation ($SO_2$) denotes the percentage of oxygenated hemoglobin out of the total present hemoglobin. Muscle oxygenation ($SmO_2$) is the term used here to indicate the oxygen saturation in the muscle.

Muscles at any time, and especially when exercised, require oxygen for energy production, and therefore $SmO_2$ is a parameter that encapsulates the metabolic state of the muscle. Specifically, it describes how much oxygen is present in the muscle and when oxygen consumption exceeds the supply. Lactic acid build-up in the blood is an indirect measurement of oxygen deficits after a muscle was in an anaerobic state, as anaerobic glycolysis results in the excretion of lactate into the blood stream.

BRIEF SUMMARY

According to an aspect of the present application an optical device is provided, comprising a wearable housing; a plurality of optical sources in the wearable housing; and a plurality of optical detectors in the wearable housing and including at least three optical detectors arranged substantially in a linear arrangement.

According to an aspect of the application, an optical device is provided, comprising a plurality of optical sources arranged substantially in a linear arrangement along a first direction, and a plurality of optical detectors arranged substantially in a linear arrangement along a second direction approximately perpendicular to the first direction. Methods of assessing hemoglobin concentration based on signals detected by the optical device are also provided.

According to an aspect of the application, an optical device is provided, comprising: a wearable housing; an optical source array in the wearable housing including a plurality of optical sources; and a plurality of optical detectors in the wearable housing including at least three optical detectors arranged substantially in a linear arrangement. The at least three optical detectors include a first optical detector disposed a first distance from the optical source array, a second optical detector disposed a second distance greater than the first distance from the optical source array, and a third optical detector disposed a third distance greater than the second distance from the optical source array.

According to an aspect of the application, a wearable optical monitor is provided, comprising: an item of clothing; an optical detector module embedded in the item of clothing and including a linear arrangement of optical detectors; and a control module coupled to the optical detector module and configured to receive output signals from the optical detectors of the optical detector module.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Figure 1A:
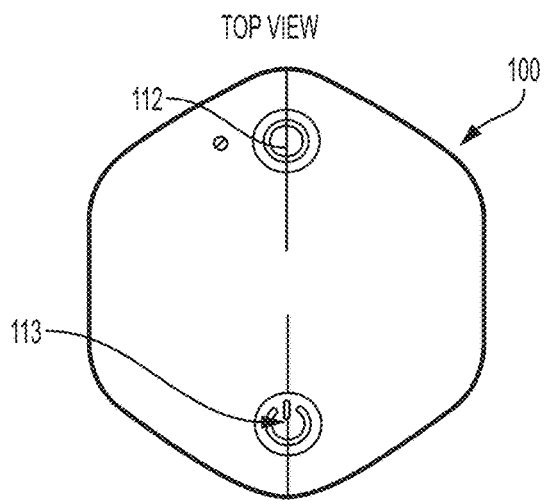
FIG. 1A is a schematic view from a first perspective of an optical device for detecting optical signals indicative of muscle oxygenation, according to a non-limiting embodiment of the present application.

Aspects of the present application relate to a wearable optical device for detecting muscle oxygenation, processes for determining muscle oxygenation based on optical signals detected by the optical device, and apparatus and methods for monitoring physical performance based on data produced by the optical device and providing input to a user, for instance when engaged in physical activity or when at rest. Applicant has appreciated that monitoring muscle oxygenation during physical activity may provide valuable insight into physical performance, particularly for those engaged in high endurance activities such as long distance running, biking, and swimming. Muscle oxygenation may provide an indication of whether muscle is aerobic, close to an anaerobic threshold, or anaerobic, and thus may be relevant to whether an athlete is performing optimally. By contrast, conventional techniques for assessing physical performance, including heart rate monitoring, provide different information and are inadequate to assess performance of muscle.

Applicant has further appreciated that conventional techniques for assessing oxygenation, such as pulse oximetry, are inadequate for assessing muscle oxygenation. Accordingly, an aspect of the present application provides an optical device suitable for collecting data representative of muscle oxygenation and/or hemoglobin concentrations during physical activity. The optical device is wearable in at least some embodiments. For example, it can be being positioned on a user's leg or arm. Thus, aspects of the present application provide a wearable fitness sensor which may assess the user's muscle oxygenation and/or hemoglobin concentrations and therefore provide an indication of the user's physical state and performance.

Aspects of the present application relate to a wearable optical device configured to emit optical signals into the muscle of a user and collect return signals in response to such emission. The wearable optical device may serve as a fitness device in at least some embodiments, being configured to provide information about hemoglobin and/or oxygenation level within tissue. The information relating to hemoglobin and/or oxygenation level may be, in some embodiments, related to lactic acid levels, which may serve as a performance metric.

Aspects of the present application provide a processor and processing techniques for converting optical signals detected by an optical sensor into an indication of any one or more of $SmO_2$, oxygenated hemoglobin concentration ($HbO_2$), deoxygenated hemoglobin concentration (Hb), or total hemoglobin concentration (HbT). $SmO_2$ represents a ratio of $HbO_2/HbT$. The optical sensor may be of the type(s) described herein, although alternatives are possible. In some embodiments, the processor may be part of the optical sensor, although in other embodiments the data collected by the optical sensor may be transferred to an external processor, such as a computer, smartphone, tablet, sports watch, or other processing device. The processing may take into account structural features of the optical sensor, including the positioning of optical sources (also referred to herein as "emitters") and optical detectors of the optical sensor.

Aspects of the present application provide apparatus and methods for providing input on physical performance to an individual. In some embodiments, a plan is provided to the individual based on the assessment of physical performance. A wearable optical sensor of the types described herein may be used to collect data indicative of any one or more of $SmO_2$, $HbO_2$, Hb, or HbT, although sensors of alternative designs may be employed in some embodiments. In response to receiving the data, an assessment of physical performance may be made and a plan created for future activity. The assessment of performance and the plan may be presented to the individual on a smartphone, tablet, computer, or other suitable device, and in at least some embodiments may be done during exercise. The assessment may be presented visually, audibly, using a combination of the two, or in any other suitable manner. In this manner, athletes may appropriately tailor their training and other activities for optimal efficiency.

The aspects and embodiments described above, as well as additional aspects and embodiments, are described further below. These aspects and/or embodiments may be used individually, all together, or in any combination of two or more, as the application is not limited in this respect.

Figure 1B:
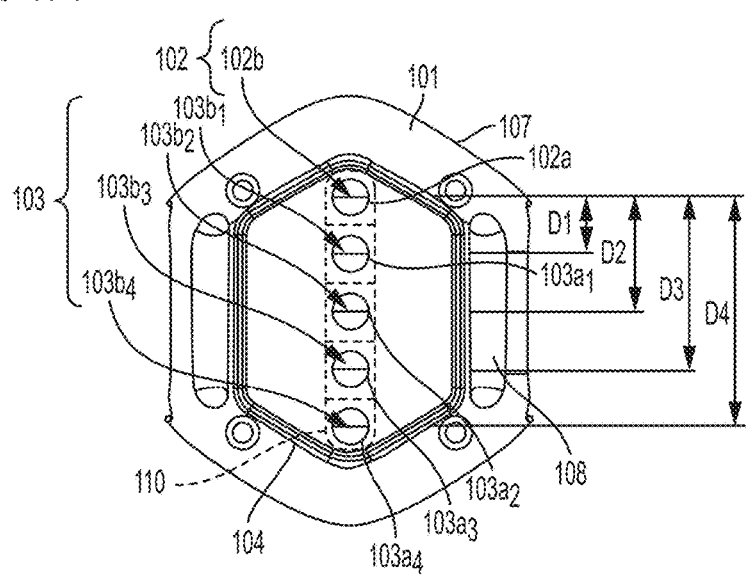
FIG. 1B is a schematic view of the optical device of FIG. 1A from an opposing view.

As described, according to an aspect of the present application, a wearable optical sensor is provided for detecting optical signals indicative of any one or more of $SmO_2$, Hb, $HbO_2$, or HbT. FIGS. 1A and 1B illustrate views of opposing sides of a wearable optical device 100 according to a non-limiting embodiment of the present application, with FIG. 1C providing a perspective view and FIG. 1D providing an exploded view. The wearable optical device 100 includes a casing 107 having such a size that a human user can wear the casing 107 on a portion of the user's body, such as the leg. For example, the casing 107 may have a maximum dimension less than 20 cm, less than 15 cm, less than 10 cm, less than 80 mm, less than 60 mm or any value or range of values within such ranges. An example of the positioning of the sensor is illustrated in connection with FIG. 4B, described further below. The casing 107 has a back side 101 proximate the user's body and a front side 106 distal the user's body during use.

FIG. 1B shows a back side 101 of the wearable optical device 100. The optical device includes multiple optical sources and multiple optical detectors. In the illustrated non-limiting embodiment, the wearable optical device 100 includes a light source array 102 and a detector array 103 disposed on the back side 101. The back side 101 may be in contact with the surface of a user's skin during operation, allowing the wearable optical device to transmit optical signals into muscle tissue underneath the skin surface and to collect optical signals from the muscle tissue.

In the illustrated embodiment, the optical emitters may be recessed relative to the surface of the back side 101 which contacts the user. With respect to the non-limiting example of FIG. 1B, the light source array 102 includes one or more emitters forming an emitter array 102b disposed within an emitter recess 102a. In alternative implementations, emitters may have respective recesses in which they are disposed. The emitter recess 102a may optically isolate the emitters from the detectors, such that the optical signals transmitted from the emitter array 102b do not directly enter the detectors of detector array 103 without passing through the tissue of the user. In some embodiments, the walls of the emitter recess 102a may include light isolation material to provide an improved light isolation between components on the back side 101. In some embodiments, the light isolation material may comprise compressive foam material, although other materials are possible.

According to an embodiment, a filter may be disposed covering the emitters, such as covering emitter array 102b. For example, the filter may cover the emitter recess 102a. The filter may be considered a window or cover and may perform a desired optical function, such as filtering undesired emissions or diffusing emitted light. A non-limiting example is described in connection with FIG. 2A.

Figure 2A:
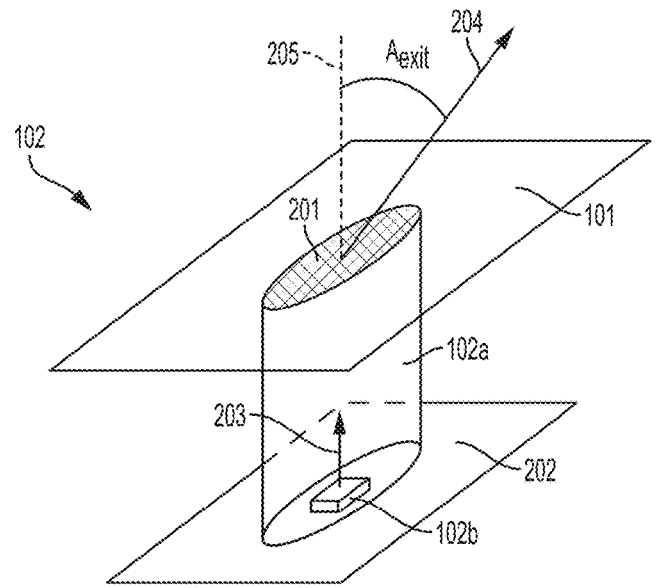
FIG. 2A shows a simplified perspective view of an emitter configuration for an optical device of the type shown in FIG. 1A, according to a non-limiting embodiment of the present application.

FIG. 2A shows a simplified perspective view of the illustrative emitter recess 102a of FIG. 1A. In this example a window filter 201 is attached to the opening of the emitter recess and is configured to selectively modify the optical signals 203 emitted from the emitter array 102b in any suitable way to facilitate a spectrum measurement. In one embodiment, the window filter 201 may comprise a tinted filter to modify the spectrum of the optical signals emitted into the user. In another embodiment, the window filter 201 may comprise a roughened texture to diffuse optical signal 203 by scattering so that light signals 204 exit the window filter along a plurality of angles $A_{exit}$ relative to an axis 205 normal to the window filter. The plurality of exit angles $A_{exit}$ may comprise a maximum angle of at least 30 degrees, at least 45 degrees, at least 60 degrees, at least 90 degrees, between 20 and 90 degrees, or any value or range of values within such ranges.

Figure 2B:
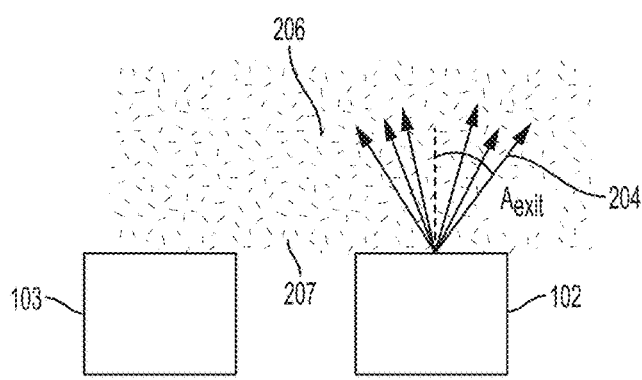
FIGS. 2B and 2C show cross-sectional views of emissions from an emitter in accordance with an aspect of the present application.
Figure 2C:
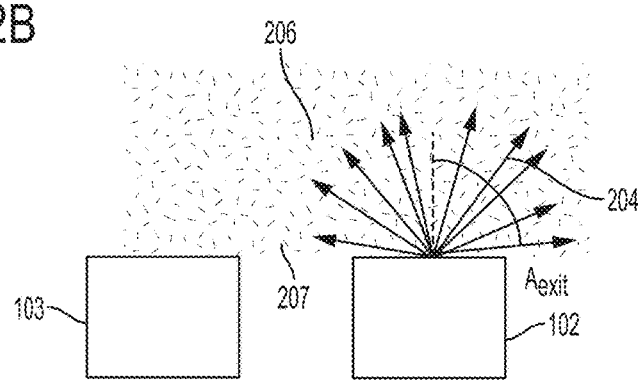

As previously described, the optical device 100 contacts a user during use in at least some embodiments. For example, the optical device 100 may be configured such that the back side 101 contacts a user's skin in use. FIGS. 2B and 2C show a cross-sectional view of the optical signals 204 emitted into a medium 206, such as a human tissue (e.g., muscle), from the light source 102 both without window filter 201 (FIG. 2B) and with window filter 201 (FIG. 2C). In the illustrated examples, the window filter 201 is assumed to be a diffuser, although not all embodiments are limited in this respect.

As can be seen from FIGS. 2B and 2C, in the absence of window filter 201 the emitted light signal 204 may be focused over a relatively narrow exit cone of maximum exit angle $A_{exit}$ (FIG. 2B). In comparison, the use of window filter 201 diffuses the light signal 204, resulting in the light signal 204 exhibiting an exit angle $A_{exit}$ of greater maximum extent than in the absence of the window filter 201 (FIG. 2C). For example, in the context of FIG. 2C, $A_{exit}$ may extend up to approximately 90 degrees and may simulate uniform semi-spherical light scattering from a point light source in a homogenous medium. The more diffused light signal 204 in FIG. 2C comprises more light components with emission directions along the surface 207 of the medium 206 toward the direction of a detector array 103 along the same surface 207 and requires less scattering distance to reach the detector array 103.

In addition to performing an optical function, window filter 201 may physically seal the cavity containing the emitter array, and thus may protect the emitter array from damage from environmental factors such as moisture. In one embodiment, the window filter may be attached to the emitter recess 102a using optical glue or any other suitable optically transparent adhesive or fastener. In an alternative embodiment, the window filter may be molded directly into the housing, achieving a mechanical bond by appropriate design of the window filter and housing, as well as a chemical bond achieved through adhesion of the plastics during the molding process.

The emitter array 102b may include a plurality of individual light emitters arranged to fit within the recess 102a. The emitters may be any suitable type of emitters, such as light emitting diodes (LEDs). In some embodiments, the emitters of the emitter array 102b may be narrow-band light sources. As used herein, "narrow-band" means that substantially all of the optical signal energy is concentrated at one narrow wavelength band centered around one peak wavelength. For example, greater than 90% of the signal intensity is within +/−10% of a nominal peak wavelength, or less (e.g., +/−6%). In one embodiment, the emitter array 102b may be narrow-band light sources that emit light signals with a plurality of peak wavelengths to provide multi-colored illumination. In contrast to using a broadband light source with a spectrometer to get spectral information, embodiments of the present application use multiple different colored narrow-band light sources such as narrow-band LEDs. The use of multiple narrow-band light sources allows for collection of spectral information without using large and expensive conventional spectrometers with a broadband light source.

As a non-limiting example, the emitter array 102b may include a plurality of narrow-band LEDs that emit light signals with two peak wavelengths at 660 nm and 855 nm in the red/infrared spectrum. Those wavelengths may be selected based on the hemoglobin absorption spectra with respect to oxygenated and deoxygenated hemoglobin. In other embodiments, a greater number of peak wavelengths may be used to obtain a higher quality spectrum with less noise. For example, the emitter array 102b may be narrow-band LEDs that emit light signals comprising two, three, four, or five different peak wavelengths.

While 660 nm and 855 nm are two non-limiting example, it should be appreciated that other wavelengths may be used. For example, one wavelength in the range of 650 nm to 710 nm may be used and another wavelength in the range of 820 nm to 860 nm. More than one wavelength in each of those ranges may be used in some embodiments. In some embodiments, an additional wavelength in the range of 950 nm to 1000 nm may be used. Still other combinations of wavelengths are possible.

When narrow-band light sources are used, a single wavelength may be emitted at a single time, as an example. A detector may be used to measure the intensity of a reflected light from the test subject for that wavelength. Then, a different wavelength may be emitted and the light reflected from the subject measured. In this manner, the optical device may provide measurements of portions of the reflection spectrum (which may be referred to as "slices" in some embodiments). Also, using the optical device 100, in one embodiment, a spectrum of detected light dependent on distance may be collected. By shining light signals from narrow-band light sources into a subject and measuring the intensity of the light signals reflected from the muscle tissue underneath the skin at several different locations with varying distances from the light sources along the skin (e.g., distances D1-D4 in FIG. 1B), the spectral intensity corresponding to various portions of the spectrum, is obtained at each measurement location, which when combined with the distance from the light source allows for determination of hemoglobin and/or muscle oxygenation levels.

Figure 1C:
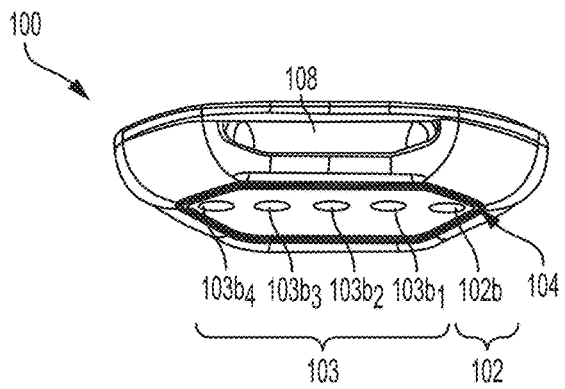
FIG. 1C is a perspective view of the optical device of FIG. 1A.
Figure 1D:
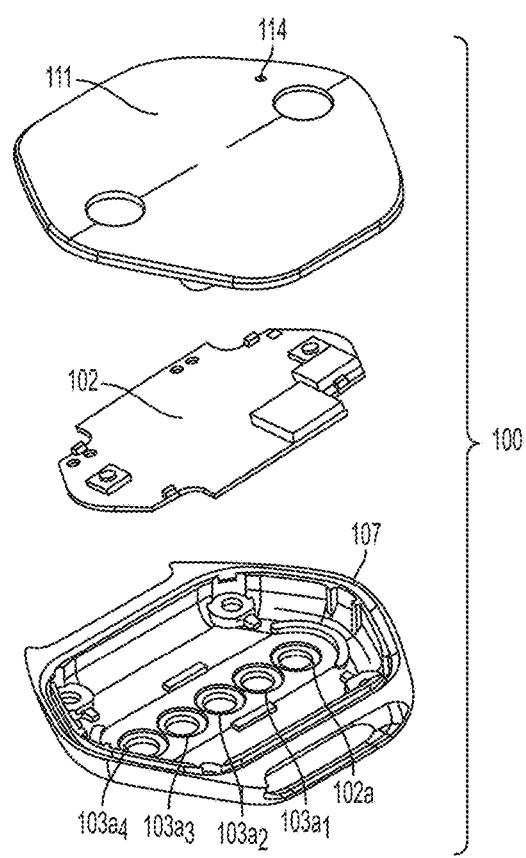
FIG. 1D is an exploded view of the optical device of FIG. 1A.

In some embodiments, the emitters of emitter array 102b may be attached to a printed circuit board (PCB), such as PCB 202 shown in FIG. 1D and FIG. 2A. In one embodiment, the emitter array 102b may be narrow-band LEDs powered by a low noise analog LED driver on the PCB 202 as adjustable current sources to set the emitted light intensity level. Other manners of housing the emitters within the optical device 100 are also possible.

The emitters of the emitter array 102b may be arranged suitably to provide desired distances between the emitters and the detectors of the optical device 100. For example, the emitters of the emitter array 102b may be arranged close together to serve effectively as a point source in some embodiments. That is, the emitter(s) may occupy a single position of the optical device, with the detectors spread over varying distances. The emitters array may occupy less than 20 mm in some embodiments, less than 10 mm in some embodiment, or other sizes serving effectively as a point source. For example an emitter array of two emitters may have a lateral extent of 10 mm or less in some embodiments. In other embodiments, the emitters of the emitter array 102b may be arranged linearly, for example occupying a total lateral extent of less than 20 mm or any value within that range. As a non-limiting example, the emitter array 102b may include four emitters arranged linearly, with the linear arrangement of the emitters being angled with respect to a linear arrangement of optical detectors. For example, the emitters may be arranged in a line substantially perpendicular to a line along which the detectors are arranged. In some embodiments, the emitters may be positioned toward an edge of the optical device 100 and the detectors located centrally, such that the path from the emitters to the detectors points inward. Such a configuration may reduce the impact of stray light.

The detectors of the optical device 100 may be arranged suitably to provide desired distances relative to the optical emitters. In the examples in FIGS. 1B and 1C, a detector array 103 is provided including a plurality of detectors 103b$_1$, 103b$_2$, 103b3, and 103b$_4$ arranged substantially linearly on a path that originates from the location of the emitter array 102b. In the illustrated example, the linear arrangement of detectors is substantially perpendicular to the linear arrangement of optical emitters. Although four detectors 103b$_1$-103b$_4$ are shown, any other suitable number may be included. In some embodiments, the number of detectors included is selected to provide at least three distinct emitter-detector distances. For example, detector 103b$_2$ is a different distance D2 from the emitter array 102b than is detector 103b$_1$ (which is displaced from the emitter by a distance D1) and also a different distance than is detector 103b$_3$ (which is spaced from the emitter by a distance D3) and detector 103b$_4$ (which is spaced from the emitter by a distance D4). The three or more emitter-detector distances may facilitate determination of $SmO_2$, $HbO_2$, Hb, and/or HbT. The distances D1-D4 may assume any suitable values to facilitate determination of the desired characteristics (e.g., $SmO_2$) while in at least some embodiments providing a compact size suitable for implementation in a wearable housing. For example, D1 may be greater than 5 mm and D4 may be less than 50 mm in some embodiments, with D2 and D3 falling within those ranges at any suitable spacing. That is, in some embodiments, each of D1-D4 may be between 5 mm and 50 mm in some embodiments, although other values are possible. In some embodiments, the optical device 100 includes five or fewer detectors, and in some embodiments only four detectors.

In an alternative arrangement, detectors may be provided with different spacing on both sides of the LEDs. According to a further alternative, multiple linear detector arrays may be provided in different spatial directions. This may allow for mapping of the spatial distribution of the muscle oxygenation and/or hemoglobin concentration over the muscle to examine a larger portion of the tissue. This may also provide better SNR, for example by averaging out scattering from varicose veins, provide robust measurements in the presence of superficial skin lesions, and examine the heterogeneity of the $SmO_2$ (or Hb or $HbO_2$ or HbT) distribution in the tissue.

In this example, each detector is disposed inside a detector recess such as 103a$_1$ to expose the detector for detection of a light signal. Respective recesses may be provided, such as 103a$_1$-103a$_4$. The detector recesses such as 103a$_1$ also provide light isolation of the optical signals entering the detectors from other components exposed on the back side 101. In some embodiments, it may be preferred that the detector array 103 collects substantially light signals from the skin surface (or, more generally, tissue) while minimizing light transmitted directly from the emitter array 102b to the detector array 103, to minimize stray background signals. Further according to some embodiments, it may be preferred that all light signals entering a particular detector substantially correspond to a light signal reflected from a test subject surface immediately adjacent the detector recess in which the detector is disposed, to provide a more accurate correlation of detector signal versus location of the detector. Therefore it may be preferred that the amount of stray light between different detector recesses be minimized. Although not shown, the walls of the detector recesses such as 103a$_1$ may include light insulation material to provide an improved light isolation between each detector and between the detectors and the emitter array. In some embodiments, the light insulation material may comprise compressive foam material. In some embodiments, as shown in FIG. 1B, an isolation wall 110 may optionally surround the emitter array 102b and detectors of the detector array 103 to provide light isolation. The wall 110 is shown in dashed lining because of its optional nature. The wall 110 may be formed from the casing material or from any other suitable material for blocking light.

In the example in FIG. 1B, each detector recess such as 103a$_1$ may include a window filter covering the opening area of the detector recess and forming a cavity containing the detector such as 103b$_1$. The window filter may be, and in some embodiments is, configured to modify the optical signals entering the detector such as detector 103b$_1$ in any suitable way to facilitate a spectrum measurement. In one embodiment, the window filter may comprise a tinted filter to modify the spectrum of the optical signals transmitted through. In some embodiments, the window filter may optionally include one or more additional functions from focusing (e.g., a Fresnel lens) and beam steering/spatial filtering. When included, the window filter may also physically seal the cavity containing the detector to protect the detector from damage from environmental factors such as moisture. In one embodiment, each window filter may be attached to the detector recess using optical glue or other suitable adhesive or fastener. In an alternative embodiment, the window filter may be molded into the housing, achieving a mechanical bond by appropriate design of the window filter and housing, as well as a chemical bond achieved through adhesion of the plastics during the molding process.

The optical detectors 103b$_1$-103b$_4$ measure the intensity of a light signal. The detectors may be optical receivers with onboard analog-to-digital conversion that converts a light signal that enters a semiconductor junction into electrical energy and then outputs the detected light signal intensity as "counts". In some embodiments, the detectors may convert a total light signal intensity across all wavelengths into counts. As an example, the detectors may be photodiodes. The detectors may be integrating photodetectors with onboard analog-to-digital conversion, although alternatives are possible. In another non-limiting example, the detectors may be TSL2591 light-to-digital converters. The detectors may be sampled at a frequency suitable to mitigate the effects of muscle movement. For example, the detectors may be sampled at a frequency less than 10 Hz, less than 5 Hz, less than 3 Hz, less than 2 Hz, or at any sampling rate within such ranges. In an alternative embodiment, the detectors may be silicon photodiodes, with analog to digital conversion accomplished using a photometric front end with analog-to-digital converter to convert current measured from the photodiode into counts. In one non-limiting example, the photometric front end may be Analog Devices ADPD103, available from Analog Devices, Inc. of Norwood, Mass. In this example the photodetectors may be sampled at 4000 Hz, 1000 Hz, 100 Hz, 0.1 Hz, less than 4000 Hz, less than 100 Hz or any sampling rate within such ranges. In another non-limiting example, the photodiodes may be Everlight PD15-22C/TR8, available from Everlight America, Inc. of Carrollton, Tex.

In the example in FIG. 1B, a plurality of detectors such as $103b_1$-$103b_4$ are arranged substantially linearly on a path that originates from the location of the emitter array $102b$ for measurement of light signals at varying locations from the emitter array $102b$. Although four detectors $103b_1$-$103b_4$ are shown, any other suitable number may be included. In a preferred embodiment, at least three detectors are used to measure the intensity of light signals for at least three different distances from the emitter array, to provide an improved fitting of measured signals as a function of distance with a model used to provide any one or more of $SmO_2$, Hb, $HbO_2$, or HbT based on the measured intensities. In the non-limiting example in FIG. 1B, the detector-emitter distances D1-D4 are such that D4>D3>D2>D1. Providing more than three detectors may further improve the quality of measurement data.

In some embodiments, two or more of the detectors may be of different sizes than each other. Because light intensity decreases with distance from the source, detector $103b_1$ is likely to receive a greater light intensity than detector $103b_2$, while detector $103b_2$ is likely to receive a greater light intensity than detector $103b_3$, and detector $103b_3$ is likely to receive a greater light intensity than detector $103b_4$. Thus, using detectors of equal sizes and sensitivities in a configuration like that shown in FIG. 1B is likely to result in the detectors $103b_1$-$103b_4$ producing different output signal magnitudes, with the detector $103b_1$ likely to produce an output signal of the greatest magnitude and detector $103b_4$ likely to produce an output signal of the smallest magnitude among the detectors. The difference in output signal magnitudes may be substantial in some embodiments, for example amounting to an order of magnitude or more. Applicant has appreciated that such differences in magnitude can lead to difficulty in processing the received signals, for example due to constraints on the capability of the processing circuitry to handle signals of substantially different magnitudes.

Thus, according to an aspect of the present application, the detectors may be sized to produce output signals of magnitudes that are within an acceptable range of each other. For example, the detectors may increase in size the farther they are from the emitter array $102b$. That is, detector $103b_2$ may be larger than detector $103b_1$, detector $103b_3$ may be larger than detector $103b_2$, and detector $103b_4$ may be larger than detector $103b_3$. In some embodiments, at least one detector is smaller in size than another detector positioned farther from the emitter array. For example, detector $103b_1$ may be smaller than one or more of detector $103b_2$, detector $103b3$, or detector $103b_4$. In some embodiments, detector $103b_2$, detector $103b3$, and detector $103b_4$ are equally sized, and are all larger than detector $103b_1$. As an alternative to using detectors of different sizes, the detectors may be sized equally but have increasing sensitivities the farther they are from the emitter array $102b$. In this manner, the detectors $103b_1$-$103b_4$ may produce output signals that are relatively close in magnitude to each other, which may simplify processing by the processing circuitry. The differences in size and/or sensitivity of the detectors may be accounted for by scaling the detector output signals based on the known differences in size/sensitivity. For example, the detector output signals may be normalized in some embodiments.

In some embodiments, the optical detectors are arranged and configured electronically to be operated synchronously with the emitters. An example of a device which may be used for such operation is the ADPD103 photometric front end, listed above. In some embodiments, synchronously operating the emitters and detectors of a photometric front end or other optical device involves aligning the integration (time) windows with the emitter (time) windows for accurate measurement of the optical signal. In some embodiments, emitters and detectors may be operated synchronously with the emitter windows and integration windows not precisely aligned, and the measured values may be mapped to the true values. Misalignment of the integration windows and emitter windows of a photometric front end or other optical device may occur, for example, if the windows of the measurement channels are not individually controllable, but rather are set as a group. In such circumstances, the alignment of integration and emitter windows may be imprecise for one or more measurement channels, resulting in measurement error, the degree of which may depend on the degree of misalignment between the integration and emitter window for a particular channel. Mapping the measured optical signal intensity values when the integration window and emitter window are misaligned to the true values may provide improved performance, and represents a calibration of the system. The functional form of this mapping may be a polynomial, where the order, and coefficients of the polynomial that accomplish the mapping can be determined through calibrating the sensor against samples with known optical properties. If the difference in measured and true values is due primarily to hardware configuration, such as routing of a circuit board, then calibrating (mapping) as described above for a single unit may apply equally well for all other units of the same kind.

Any suitable spacing, or spacing combination between centers of each detector on the substantially linear path and between the first detector of the plurality of detectors and the emitter array may be provided to arrange the detectors and emitter array on the back side 101 of the wearable optical device 100. In a non-limiting example, the detectors may be spaced 10 mm apart between centers of each adjacent detector and between the center of the first detector of the plurality of detectors and the emitter array. In other embodiments, smaller spacing may be used to allow for inclusion of a greater number of detectors, such as a spacing of 8 mm. For example, the detectors of FIG. 1B may be spaced from the emitters by 8 mm, 16 mm, 24 mm, and 32 mm, respectively. In some embodiments, the spacing between neighboring detectors may be between 5 mm and 20 mm, less than 5 mm, less than 1 mm or any distance or range of distances within such ranges. In some embodiments, the detectors may be pixels of an imaging device, such as a charge-coupled device (CCD) imager.

One or more of the detectors may serve to provide a reference signal. For example, in the context of optical device 100, the detector closest to the emitter $103b_1$ may provide a reference intensity against which the intensities measured by detectors $103b_2$-$103b_4$ are measured. In this manner, control over and knowledge of the variations in intensity of the signals emitted by the emitters may be provided, simplifying the device design and operation. In such configurations, the detector serving as the reference may not contribute to the unique emitter-detector distances, although in other embodiments it may. That is, in the example of FIG. 1A, three unique emitter-detector distances are provided by detectors $103b_2$-$103b_4$, while detector $103b_1$ provides a reference (or baseline) for the other detectors.

Applicant has appreciated that stray light may undesirably impact the performance of an optical device such as optical device 100. For example, the optical device 100 may be used in situations in which sunlight or other environmental light is present. Detection of such environmental light could negatively impact device performance. Accordingly, as illustrated in FIGS. 1B and 1C, the optical device may include a seal ring 104 configured to prevent environmental light or other stray light from unintentionally being detected by the detectors of the optical device 100. The seal ring 104 may be a raised portion of the casing 107, formed by a continuously raised portion around the periphery of the back side 101 as shown. The height of the seal ring may be less than 1 mm, less than 2 mm, or any other suitable height. The seal ring may be constructed from substantially the same material as the casing material on the back side 101, or it may be constructed from any other suitable material for providing a seal when in contact with a surface of the user. In some embodiments, the seal ring is constructed with a dimension that maintains substantially the overall small footprint of the wearable optical device. In some embodiments, when the wearable optical device is used on a user, the back side 101 is placed facing the skin of the user and the seal ring 104 is in contact with the skin of the user forming a complete seal with no gaps such that no ambient light reaches any of the detectors such as $103b_1$ to reduce stray background signal and improve SNR of the detected signals. The seal ring may serve additional functions, such as helping to retain the optical device in position on the user, prevent moisture (e.g., sweat or rain) from interfering with the optical operation, or other functions.

Other features of the optical device 100 include optional buttons, lights, and openings for a strap or other fastening mechanism. Referring to FIG. 1A, the optical device 100 may include buttons such as a "record" button 112 to allow for recording of data and a "power" button 113 to allow for controlling the ON/OFF state of the optical device 100. Other buttons, switches, knobs, or user interface elements may optionally be included.

The optical device 100 may optionally include an output indicator, such as a light. FIG. 1D illustrates an LED status indicator light 114.

As will be described further below in connection with FIGS. 4A and 4B, the optical device 100 may be wearable and may include features allowing it to be fastened to a user. An example of a fastening mechanism is a strap, and thus the casing 107 may include suitable features for holding the strap, such as one or more slots 108. In some embodiments, a strap 105 is used to attach the wearable optical device 100 to the user's skin and to provide compression force to ensure a tight seal from the seal ring 104.

Figure 5:
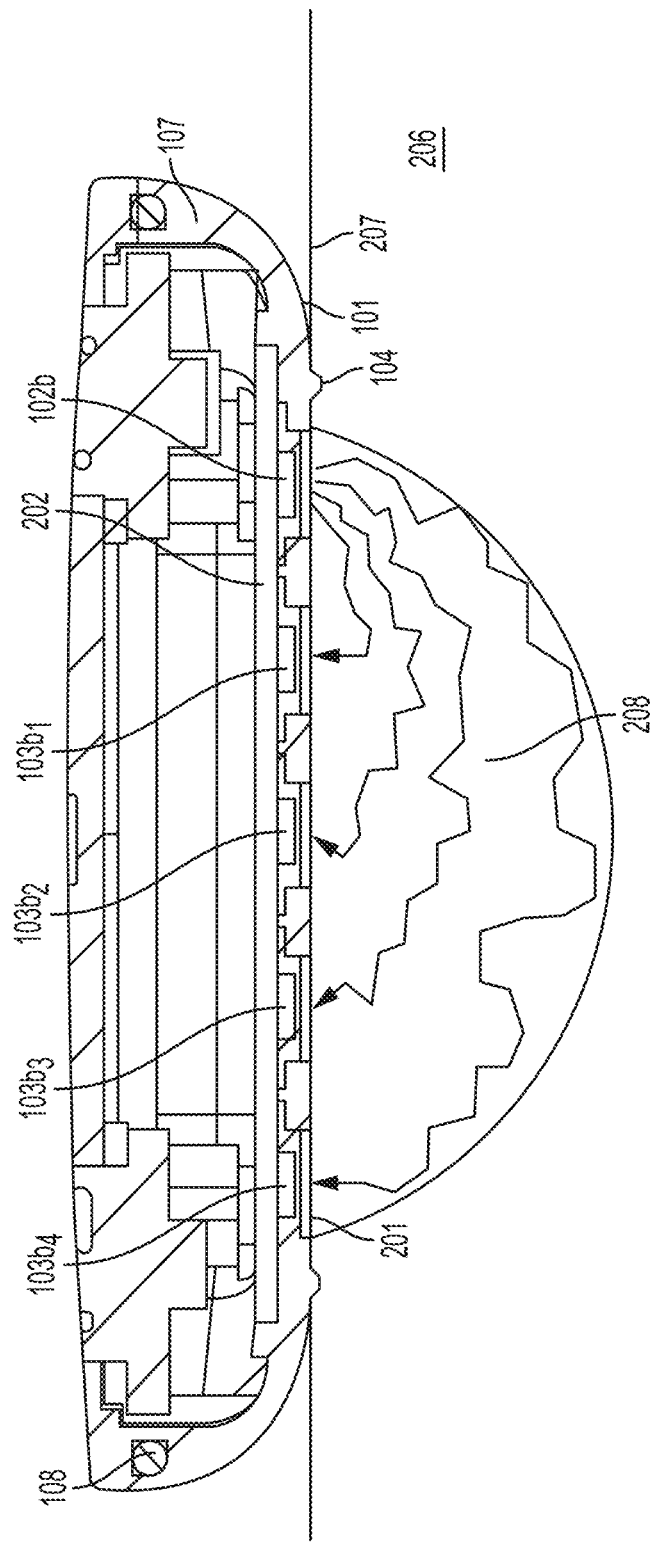
FIG. 5 is a cross-sectional view of an optical device of the type illustrated in FIG. 1A in contact with a user, according to a non-limiting embodiment of the present application.

FIG. 5 illustrates a cross-sectional view of the optical device 100 in contact with a user. A suitable fastening mechanism such as a strap 105 may be used in combination with slots 108 to secure the optical device 100 such that the seal ring 104 on the back side 101 is pressed into and forms a ring of indentation in the surface 207 (e.g., the user's skin) to prevent stray light from entering the components on the back side 101 of the optical device 100. During operation of the optical device in the example in FIG. 5, light signals emitted from emitter array 102b enter the medium 206 (e.g., the user's muscle tissue), scatter through the tissue via light scattering path(s) 208, and then are detected at various locations by detectors $103b_1$-$103b_4$. The detectors $103b_1$-$103b_4$ and emitter array 102b are close to the surface 207 during operation, with optical windows 201 between the detectors/emitter array and the skin. The detectors and emitter array are physically and electrically connected to a PCB 202 inside the casing 107 of the optical device.

FIG. 1D illustrates an exploded view of the optical device 100, including a front and back sides of the casing 107, with a circuit board 202 or other substrate in between. The circuit board (e.g., a printed circuit board) may support the electronics of the optical device. An example of the circuitry is described in connection with FIGS. 3A-3B.

Figure 3A:
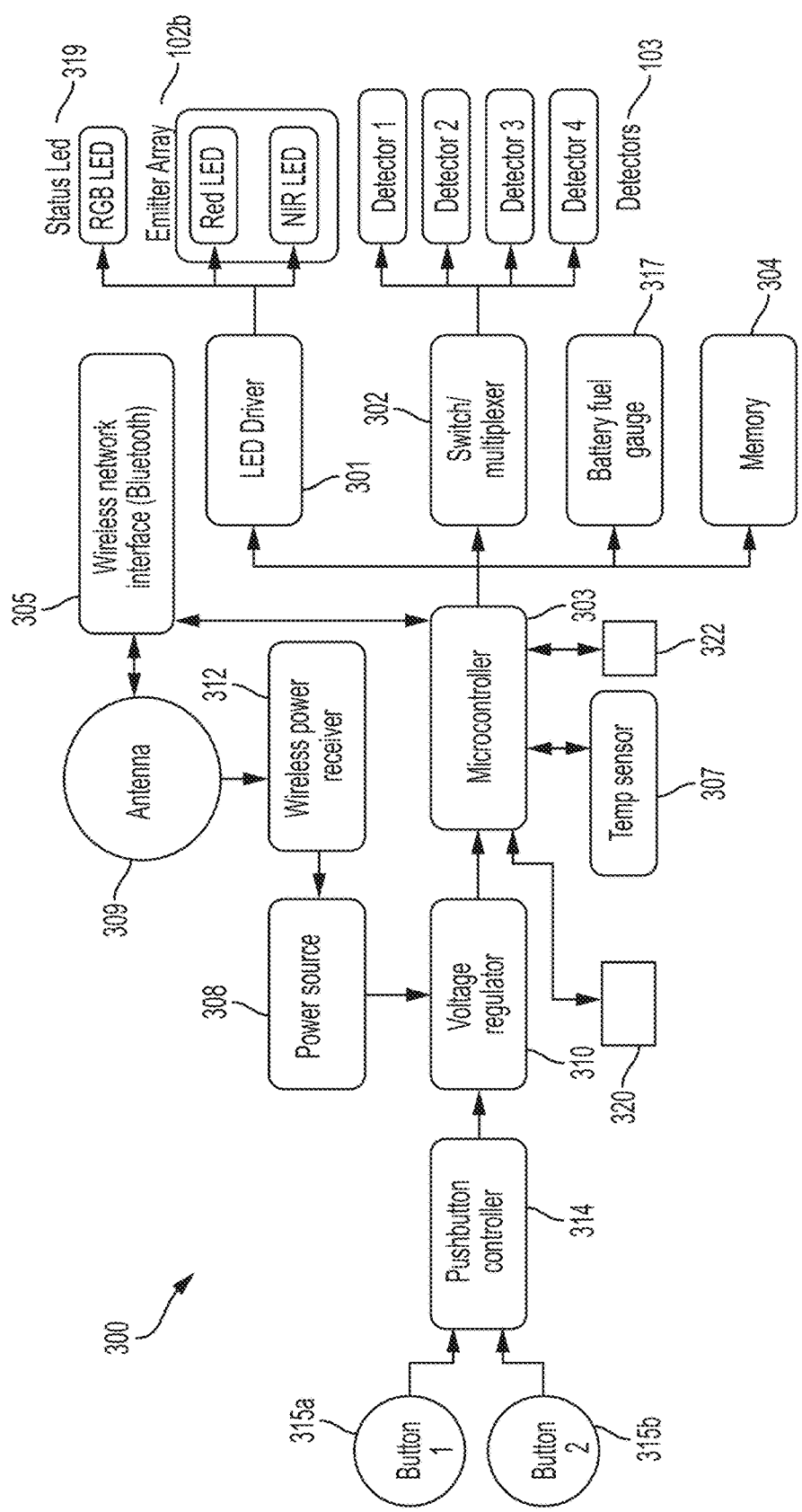
FIGS. 3A-3B are block diagrams of the circuitry of an optical device of the type shown in FIG. 1A, according to two non-limiting alternative embodiments of the present application.

FIG. 3A is a block diagram showing an internal configuration of the wearable optical device 100. A digital board 300 is provided inside the casing 107 to provide physical support and electrical connections for various components on the board.

In one embodiment, the digital board 300 may include an analog emitter source driver 301 such as an LED driver, to selectively provide power to the emitter array 102b based on communications with a microcontroller 303. In one non-limiting example, the analog emitter source driver 301 may include a low noise analog LED driver as adjustable current sources to selectively set the emitted light intensity level in narrow-band LEDs.

In the example in FIG. 3A, the digital board 300 includes a switch/multiplexer 302 to communicate to each of the detectors in 103 and selectively transmit counts data from each detector 103b to the microcontroller 303. In one embodiment, the multiplexer may be a Bus Multiplexer that communicates with the microcontroller 303 to send detector data to the microcontroller 303. In one non-limiting example, the multiplexer may be a Bus Multiplexer based on the I2C communication protocol. In some embodiments, the multiplexer 302 may be a switch.

In the example in FIG. 3A, the microcontroller 303 is configured to control the output of the light source array 102 by communicating with the emitter source driver 301. The microcontroller 303 reads and processes the detector counts by communicating with the switch/multiplexer 302. The microcontroller 303 also communicates with a memory 304, or other onboard storage device, for storing and reading data.

In the example of FIG. 3A, there may be provided at least one temperature sensor 307 for measuring temperature data and for communicating temperature data with the microcontroller 303. The temperature sensor(s) may sense skin temperature, device temperature, and/or ambient temperature. The temperature data may be used to account for temperature induced variations in operation of the device or optical behavior of the tissue in question. For example, temperature influences the emitter (e.g., LED) emissivity in terms of output power, may change the spectrum emitted, and/or the battery charge state. Accurate battery monitors may benefit from temperature data to predict how long the battery will last. Device temperature could be related to skin temperature, which might part of a parameter set used to extract body functions (e.g. blood flow). Blood flow would allow to calculate further body parameters like calorie consumption. The temperature sensor may include an analog temperature sensor probe and an analog-to-digital conversion device for processing the temperature sensor probe data into digital data suitable for communication with the microcontroller 303.

Additional sensors may optionally be included. For example, an accelerometer 320, heart rate sensor 322, or other sensor may be included. Data from such sensors may be used in combination with the optical data to assess physical activity and provide input to a user, as described further below. While the accelerometer 320 and heart rate sensor 322 are shown on the digital board 300, in alternative embodiments they may be discrete components, and the data from such sensors may be combined with the optical data by the microcontroller or an external processor.

In one embodiment, the microcontroller 303 transmits data via a wireless network interface 305 to an external device. The wireless network interface may be a Bluetooth connection, an antenna, or other suitable interface. In some embodiments, the transmitted data may be raw detector data received from the switch/multiplexer 302 or any other sensors such as the temperature sensor 307. In other embodiments the transmitted data may be processed by the microcontroller 303 in any suitable way prior to transmission. The external device may be a data storage device to store the transmitted data from the microcontroller, or a device with a processor and a user interface for interactively displaying and/or further processing the transmitted data. In one embodiment, the wireless network interface 305 is a Bluetooth Low Energy (BLE) module. In one non-limiting example, the wireless network interface 305 and the microcontroller 303 are integrated in one unitary component, such as a RFduino microcontroller with built-in BLE module, a Nordic Semiconductor microcontroller, or a Cypress microcontroller with BLE module.

The digital board 300 also includes at least one antenna 309 for wirelessly transmitting and receiving power and/or data. For example, the antenna 309 may transmit and/or receive data via the wireless network interface 305. In some embodiments, wirelessly transmitting and receiving data via the wireless network interface 305 includes encrypting and decrypting the data such that unauthorized access to the device or data on the device is prevented. In some embodiments, data may be transmitted to the microcontroller 303 via the wireless network interface 305. The data transmitted to the microcontroller may include firmware for reconfiguring the microcontroller.

In one embodiment, the memory 304 is an onboard storage chip with any suitable storage capacity for storing data received from the microcontroller 303 and/or received via the wireless network interface 305.

In the example in FIG. 3A, the digital board 300 further includes a power source 308. In one embodiment, the power source 308 is a battery. In one non-limiting example, the power source 308 is a polymer lithium-ion rechargeable battery with a voltage of approximately 3.7V.

In some embodiments, the at least one antenna 309 includes a wireless charging coil coupled to the power source 308 via a wireless power receiver 312 to charge the power source 308 from a suitable external wireless charging source. The wireless power receiver 312 may conform to the Qi standard. Voltage regulator 310 is provided in some embodiments to regulate and condition the power output of the power source 308. Wireless charging of the device may eliminate the need to provide an opening on the casing 107 to allow a power charging cable to engage in a receptacle on the digital board 300 therefore minimizing exposure to damaging environmental factors such as moisture. The capability for wireless charging also eliminates the hassle of plugging in and unplugging a power charging cable for the user, reduces metal contacts that can cause skin irritation and experience corrosion, and thus generally may render the device more robust.

In some embodiments, there may be provided buttons 315a, 315b, status LEDs 319 and a battery fuel gauge 317 on the PCB 202 that are accessible outside the casing 107 to provide interactive control and feedback for the user to operate the device.

Figure 3B:
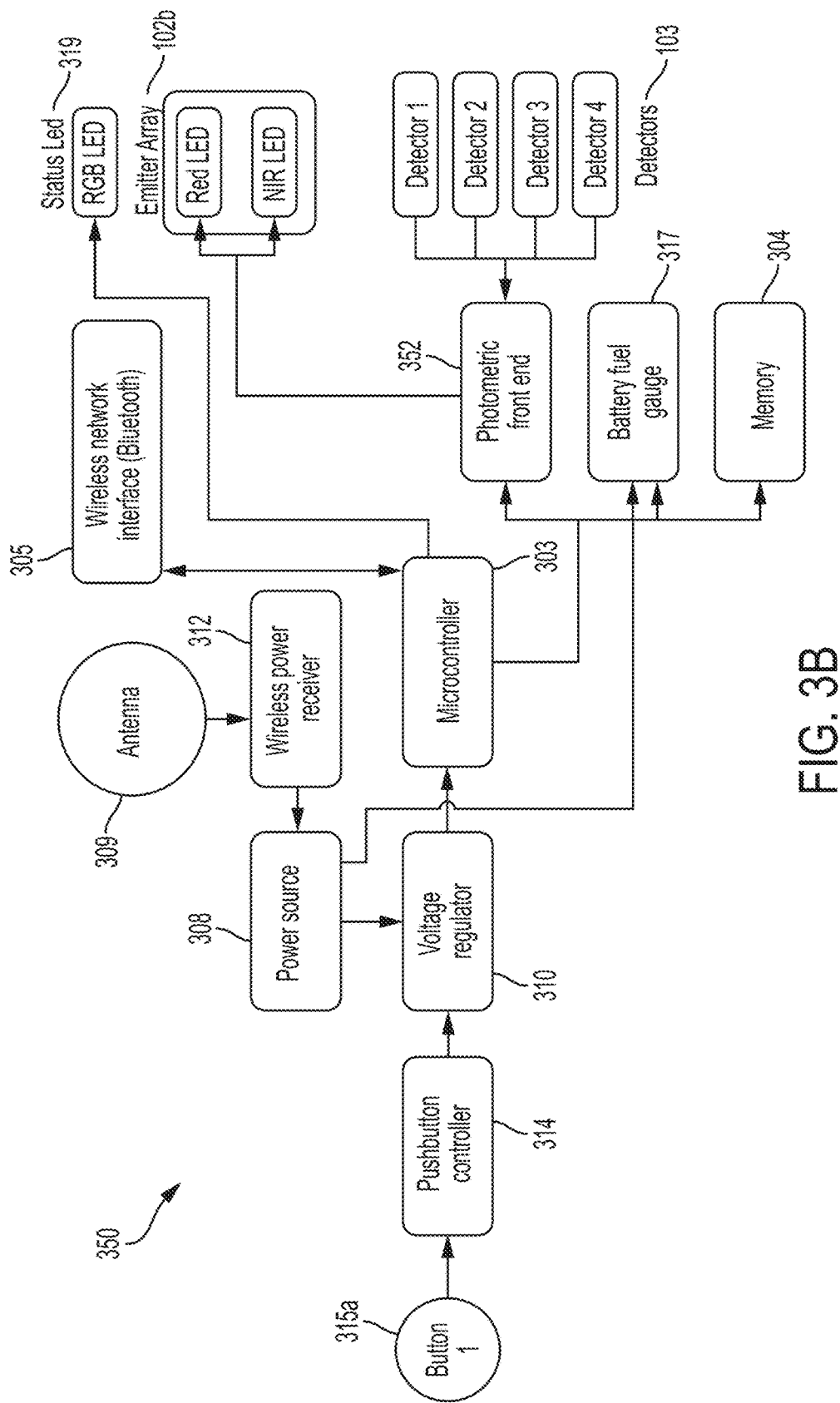

Various alternatives to the digital board 300 are possible. FIG. 3B illustrates one non-limiting alternative. The digital board 350 differs from digital board 300 in several ways. Only a single button 315a is provided on the digital board 350. The power source 308 is configured to provide an input to the battery fuel gauge 317. The temperature sensor 307, accelerometer 320, and heart rate sensor 322 are omitted. The LED driver 301 and switch/multiplexer 302 of digital board 300 are replaced by a photometric front end 352 in digital board 350. Also, the status LED 319 is driven directly by the microcontroller 303. Further alternatives are provided.

Figure 4A:
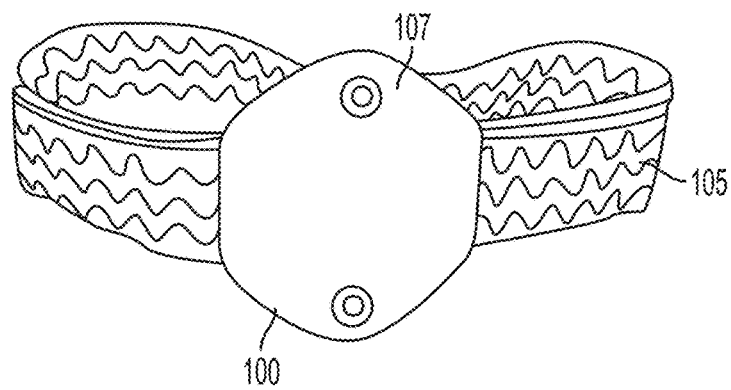
FIG. 4A shows an illustrative wearable optical device 100 with a strap 105 to secure the device 100, according to a non-limiting embodiment of the present application.
Figure 4B:
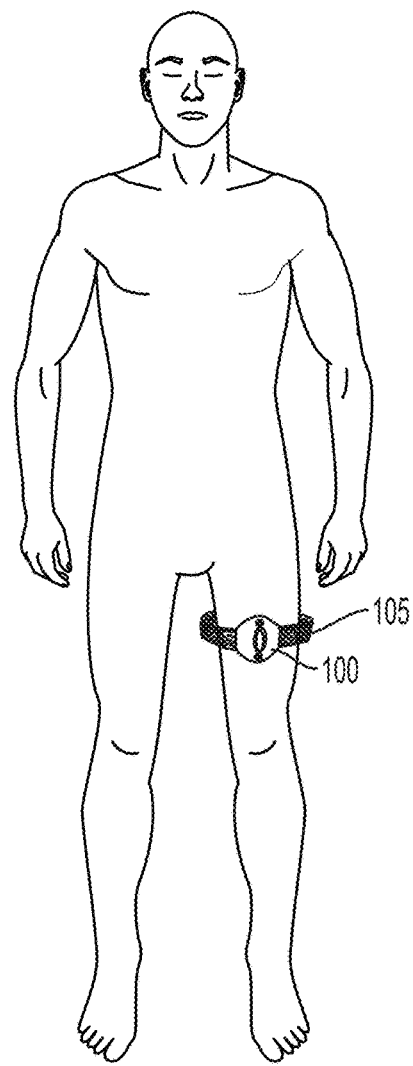
FIG. 4B illustrates the wearable optical device 100 of FIG. 4A secured to an individual.

FIG. 4A shows an illustrative wearable optical device 100 with a strap 105 to secure the device 100 for wearing on a user's body, such as a thigh as shown in the example in FIG. 4B. The strap fixes the relative position of the wearable optical device 100 to the attached body portion regardless of the motion of the body portion such as during walking, running or any activity requiring motion of the attached body portion so that the detectors on the device continuously measure signals substantially corresponding to the fixed location on the body portion. In the example in FIG. 4B, the strap 105 includes two ends, each attached to one of the two opposite sides of the casing 107 forming a loop that may wrap around a body portion. The strap 105 may include one or more mechanisms to quickly close the loop for securement to the body portion and to quickly open the loop for removal from the body portion, such as a hook and loop fastener. The quick open/close mechanism provides the user the convenience to attach and secure the wearable optical device quickly to a body portion with exposed skin, without the need to remove any piece of apparel or body covering in other portions of the body. The length of the strap 105 may be adjustable to fit around different portions of the body depending on the activity and muscle group usage, without the need to purchase additional holstering or securement components. For example, while an athlete may wish to use a wearable optical device to monitor oxygenation levels in a thigh muscle group during running or cycling, the same athlete may wish to wish to use the device on an arm during swimming.

The strap may be constructed of a flexible material to provide compression tension when securely attached to the body portion on the user. The strap may further include a mechanism to provide adjustable levels of compression to allow both a suitable level of securement to the body portion and a suitable degree of sealing between the seal ring 104 on the back side 101 of the casing 107 and the user's body. Also, the adjustable nature of the strap may facilitate achieving a comfortable fit.

While a strap is illustrated as being used to secure optical device 100 to a user, other mechanisms for securing the optical device to a user may be implemented in different embodiments.

In some embodiments, the casing 107 and the strap 105 may include additional material and/or mechanisms to allow the wearable optical device 100 to operate in harsh environmental conditions. For example, protective covers, seals, or other materials may be used to mitigate potentially negative consequences of operation in water, smoky, dusty, or high humidity environments, or environments experience high G-forces. Additional covers, seals, and protective parts may be used to further shield out ambient light and maintain a suitable temperature of the device in hot or cold environments.

An example of the operation of optical device 100 is now described, although it should be appreciated that alternative manners of operation are possible. In some embodiments, a calibration procedure is performed prior to normal operation of the device. The intensity of emitted light may decay as measured when reflected from the tissue as the distance along the surface of the tissue is increased away from the emitter. This decay can for example be exponential. Thus, in the case that the photodetectors at each measurement location are the same, the intensity measured at the closer photodiodes will be larger than that measured at the further photodiodes. Different photodetector active areas and spectral sensitivities can be used to help offset this effect, for example by using smaller photodetectors at the closer distances and larger ones further away, as described previously. However, regardless of photodetector selection, a problem may arise when applying the sensor to different users in terms of ensuring sufficient signal is measured at all detectors, but without saturating them. For a fixed photodetector configuration, the signal can be adjusted as the sensor is placed on different users by changing the output of the emitter. A calibration algorithm may be employed to automate the adjustment of the emitter intensity by starting with the emitter in a low-power configuration, so as to ensure no photodetectors are saturating. Measurements at all photodetectors are recorded, and then the emitter intensity adjusted as follows: While the maximum measured value across all of the photodetectors is below a particular threshold, increase the intensity of the emitter by a fixed amount, re-measure at each photodetector, and repeat until any photodetector exceeds the threshold, at which point reduce the intensity to the previous increment. This threshold can be set at a certain percentage of the saturation limit, for example 80 percent the saturation limit, between 70% and 85%, or any other percentage.

An example of operation of the device 100 after calibration is now described. According to an embodiment, the light source array 102 of the wearable optical device 100 includes narrow-band LEDs that emit light signals with two peak wavelengths on either side of approximately 800 nm. As an example, the LEDs may include an LED with a peak between 650 nm and 710 nm (e.g., approximately 660 nm) and an LED with a peak between 820 nm and 860 nm (e.g., approximately 855 nm). However, those wavelength ranges are examples and other wavelengths may be used. Deoxygenated blood is a stronger absorber of red light than is oxygenated blood. By contrast, oxygenated blood is a stronger absorber of near infrared (NIR) light than is deoxygenated blood. The absorption of the two is approximately the same at around 800 nm. Muscle includes a mixture of Hb as well as $HbO_2$ in the blood stream. With exercise the percentages of Hb and $HbO_2$ may change, resulting in changes in absorption of light, and therefore changes in the color of the blood. This change in the color of blood, when measured within a muscle by a suitable device, such as the types described herein, can be used to determine oxygenation levels in the muscle tissue. Thus, by analyzing the absorption of light of wavelengths below and above approximately 800 nm, determination of the percentage of oxygenated and deoxygenated blood may be made.

In operation, the optical device 100 may cycle on and off the LEDs (or other optical emitters) of different wavelengths while detecting simultaneously with all detectors. For instance, during a first cycle, one or more LEDs of a first wavelength may be activated and all detectors of the optical device may detect the emitted signals. This period may be followed by a first pause period when all LEDs are turned off. Next, one or more LEDs of a second wavelength may be turned on and all the detectors may detect the emitted signals. This period may be followed by a second pause period when all LEDs are off. The detectors may detect during any such pause periods. An example is described in connection with FIG. 6.

Figure 6:
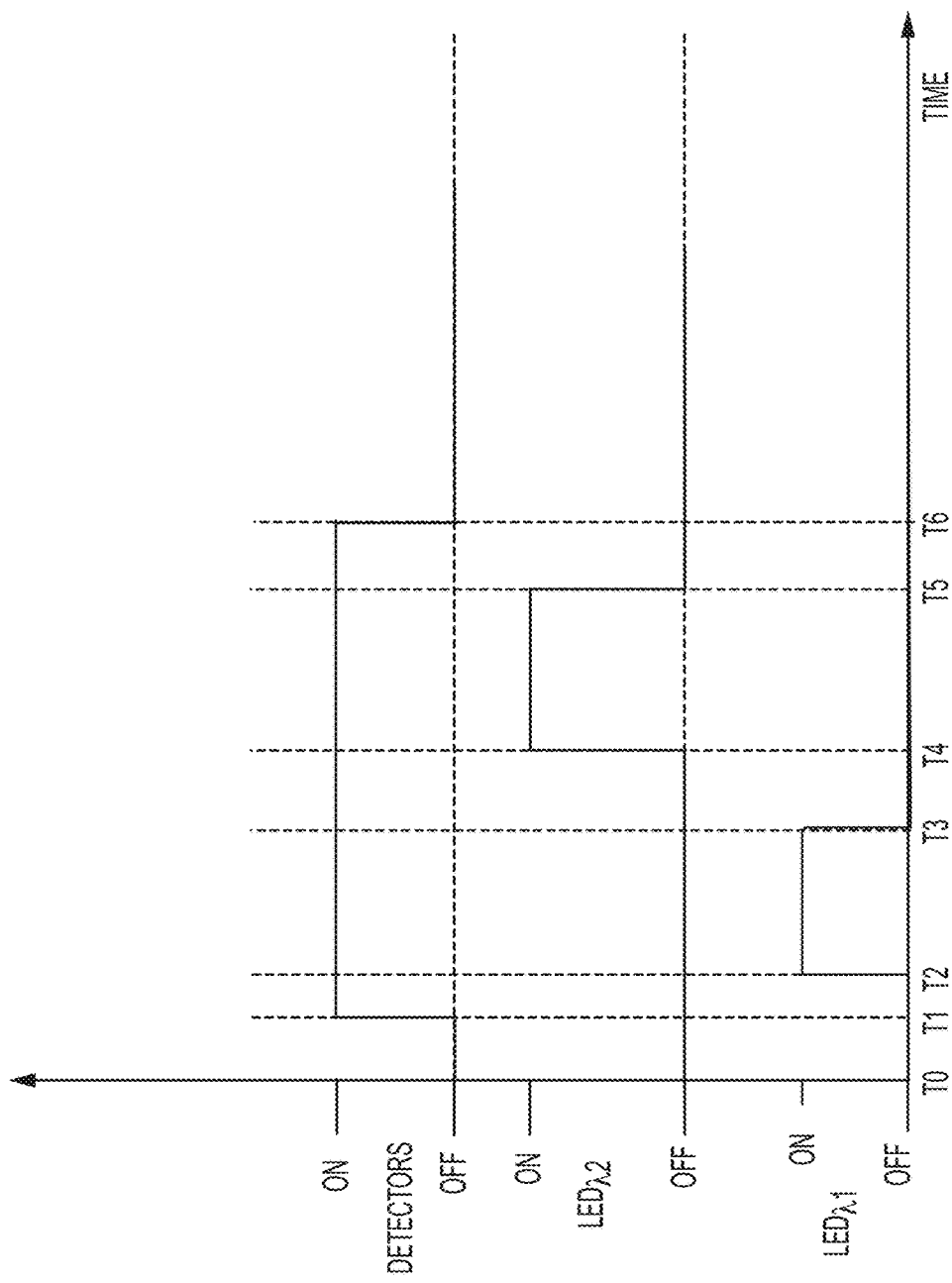
FIG. 6 illustrates a timing diagram for one manner of operation of an optical device of the types described herein.

FIG. 6 illustrates a timing diagram of one non-limiting embodiment for the operation of optical devices of the types described herein. The horizontal axis represents time. The vertical axis illustrates the ON/OFF states of LEDs of a first wavelength ($LED_{\lambda 1}$), LEDs of a second wavelength ($LED_{\lambda 2}$), and the detectors. In this non-limiting example, all LEDs and detectors may be OFF initially at time T0. This time may represent a time prior to a user initiating monitoring of the optical device. At time T1, the detectors may be turned ON. At time T2, LEDs (or other emitters) of a first wavelength may be activated, for a duration from T2 to T3. A pause period may ensue from T3 to T4 when all LEDs are OFF. As shown, the detectors may optionally remain on during this pause period.

Next, at time T4, LEDs (or other emitters) of a second wavelength may be activated, and may remain on until a time T5. At time T5, another pause period may ensue in which all LEDs are OFF. The detectors may remain ON until a time T6, ensuring that they capture signals from the entire ON duration of the LEDs.

Alternatives to the manner of operation shown in FIG. 6 are possible. Moreover, the illustrated operation may proceed for additional wavelengths of the emitters if there are more than two wavelengths, although in some embodiments the duration of the cycles and the sequence of the cycles may vary. For example, in one embodiment the sequence may be ordered as "LED 1 ON", "OFF", "LED2 ON", "OFF", etc. Each step might have a different integration time and detector gain setting, such as 300 ms, 100 ms, 200 ms, 100 ms, etc. In some embodiments, another wavelength, which may be a third or subsequent wavelength (e.g., in the range from 950 nm to 1000 nm as a non-limiting example), may be added to measure water content in the skin/tissue. In some embodiments, a separate photodetector may be included for the single purpose of continuously measuring the background. Other variations are also possible.

When any group of LEDs is turned on, the detectors in 103 record the intensity of the light signals as measured at the different distances of each of the detectors 103*b*. In some embodiments, the detected light signals at each location of the respective detectors represent measured reflectance intensity as a function of distances from the light source.

The detected intensities for the different wavelengths may be processed using any suitable algorithm, such as an exponential algorithm, an example of such processing being described below. In some embodiments, processing of the detected signal intensities includes applying a thresholding algorithm to ensure the data from any given detector is considered to be good data, by falling within a prescribed range. For example, an acceptable minimum threshold may be applied to signals detected by the detectors. Signals falling below the acceptable minimum may be discarded or otherwise omitted from subsequent processing. In such embodiments, the minimum threshold may be selected as any suitable value considered to represent an acceptable minimum for subsequent processing. The result of processing the received intensities may provide an indication of deoxygenated and oxygenated hemoglobin present in the muscle, and therefore provide an indication of $SmO_2$.

In some embodiments, it is preferred that detector data are recorded at each of the detectors at substantially the same time such that the muscle tissue condition remains substantially unchanged in order to provide an accurate calculation of the Hb and $HbO_2$ levels in the same muscle tissue at a point of time and to reduce artifacts caused by drift in a non-limiting example. Software interpolation between data points is also used in some embodiments to improve the signal-to-noise ratio, for example to improve the dark measurement data (acquired during the pause).

In some embodiments, detector data are sampled in a predefined frequency. At each sampling, detector data are recorded for a set short period of time and the recorded small group of data are processed to produce a single sampled data point to improve SNR. In some embodiments, the processing of the data may be averaging or integration. In some embodiments, sampling frequency is chosen to be fast enough to reflect time variation in a user's blood oxygenation level during the course of exercise. In some embodiments, sampling frequency is chosen to be slow enough to average out fluctuations due to user motion. In some embodiments, the sampling frequency and level of data processing may be chosen to reduce workload of the microcontroller in order to extend battery life of the wearable optical device. In a non-limiting example, detector data are sampled at frequency of 2 Hz, although other frequencies may alternatively be used, including at a frequency less than 10 Hz, less than 5 Hz, less than 3 Hz, less than 2 Hz, or at any sampling rate within such ranges. In some embodiments, the photodetectors operate autonomously, and during the data acquisition time (e.g., 100 ms) the BLE controller enters a power saving mode. After the acquisition, the controller reads out the value. Such operation can extend the battery life significantly.

A curve based on a known functional form is fit through the measured reflectance intensity versus distance data at each of the two wavelengths to obtain information about how the light through the muscle tissue is attenuated with distance at each of the two wavelengths. In some embodiments, the curve is an exponential function with the distance as part of the exponent, multiplied by a diffusion coefficient. Use of three or more detectors with three or more different distances to the light source may be preferred to fit the reflectance intensity versus distance data with the curve. The greater the number of emitter-detector distances used the better the curve fitting, including a reduction in noise. When only two detector-light source distances are provided, the resulting intensity versus distance data represent only two data points. Using two data points to fit a curve such as an exponential curve with distance in the exponent may introduce significant fitting uncertainty affecting the accuracy of the fitted data and require a number of additional assumptions about the physical configuration which may be inaccurate. Two different peak wavelengths may be used as light sources to obtain an effective attenuation coefficient at each of the wavelengths. Although in other embodiments, a greater number of peak wavelengths may be used to obtain a higher quality spectrum with less noise. Also, the use of a greater number of wavelengths would permit fitting the water content of the skin/tissue, which may be done in the alternative to assuming water content as a constant.

The curve fitting process may be repeated during each time period at which a different group of LEDs with a peak wavelength is turned on to determine an attenuation coefficient at each peak wavelength. The measurements taken during the period when all LEDs are off may be subtracted from the measurements taken while the LEDs are on, prior to performing the curve fitting.

In some embodiments, different combinations of data from the different detectors of the optical device may be used in curve fitting to assess properties at different depths within the tissue (e.g., muscle) of interest. In practice, tissue is sometimes inhomogeneous, for example varying with depth from the skin surface. As shown in FIG. 5, light detected by the various optical detectors of an optical device such as that shown in FIGS. 1B-1C and 5 may have traveled to differing depths within the tissue. Thus, the detected signals may be impacted by inhomogeneous tissue. In some embodiments, curve fitting of the detected data may be performed with different combinations of the detectors to provide an assessment of different depth-dependent tissue characteristics. Any combination of two or more of the detectors may be used. For example, in one embodiments data from detectors $103b_1$ and $103b_2$ may be used for one first curve fitting procedure. Detectors $103b_2$ and $103b_3$ may be used for another curve fitting procedure. Detectors $103b_3$ and $103b_4$ may be used for another curve fitting procedure. Alternative combinations of two or more of the detectors may be used in other embodiments. These different curve fitting procedures may yield depth-dependent information about oxygenation and/or hemoglobin concentrations within the tissue of interest. These various detector combinations may also be beneficial or even necessary in some embodiments if measurements of the adipose tissue layer located superficially to the muscle are performed. Information gathered from depth dependent measurements may provide additional health tracking metrics such as monitoring superficial fat content.

In some embodiments, using the attenuation curves and knowledge about optical properties of the muscle tissue, the absorption coefficients due to oxygenated and deoxygenated hemoglobin within the tissue may be determined. Such data, when combined with the known extinction coefficients for oxygenated and deoxygenated hemoglobin, may lead to determination of the percentage of hemoglobin that are oxygenated. In some embodiments, constant tissue scattering properties may be assumed, irrespective of the user. This means that determinations of Hb and $HbO_2$ may be approximations in some embodiments.

Aspects of the present application relate to methods of processing detected optical signals, such as those detected by optical device 100, to assess oxygenation level and/or lactic acid level within the user's muscle. A correlation between lactic acid threshold and oxygenation may be derived in some embodiments. The transmissivity of light through the muscle may be modeled as exponentially decaying quantity, decaying over distance. According to an aspect of the present application, optical intensity is detected at three or more distances from an optical emitter, and at two or more wavelengths for each such distance. Two or more wavelengths are used because of the two unknowns, Hb and $HbO_2$. Using that detected data, the percentage of oxygenated and deoxygenated hemoglobin in the muscle may be determined, thus providing an indication of $SmO_2$.

The processing of the data may be done on the optical device 100, for example by the microcontroller 303. In alternative embodiments, raw data detected by the optical detectors of the optical device may be transmitted to an external processor, such as a smartphone, tablet, computer, or other processing device which may calculate the percentage of oxygenated and deoxygenated hemoglobin in the muscle. The calculations may be performed substantially in real time during use of the optical device 100, at periodic intervals during use, or subsequent to use.

The processing described above may be sufficiently simple to be capable of being performed quickly, and on the optical device itself. In this manner, the optical device 100 may be of increased value to a user, such as an athlete, in getting timely feedback on physical performance. The calculations may avoid costly computations such as Monte Carlo simulations, the use of look-up tables requiring a large amount of stored data, or processor-intensive techniques.

Figure 7:
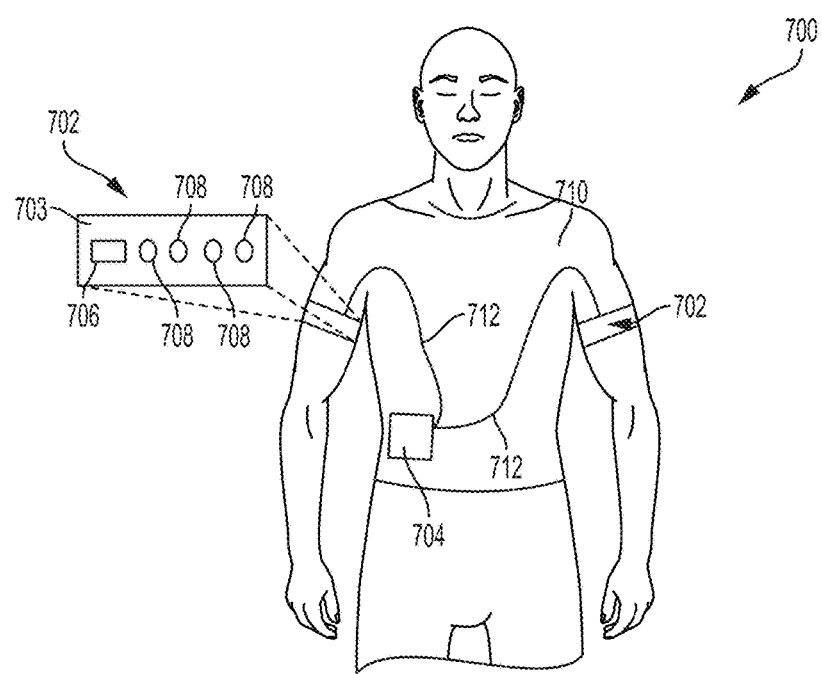
FIG. 7 illustrates a distributed optical device including emitter/detector strips and a control module.

According to an aspect of the present application, an optical device configured to detect signals which may be used to assess any one or more of Hb, $HbO_2$, HbT, or $SmO_2$ may be configured to be implemented in a garment, such as a shirt. FIG. 7 illustrates an example of a system 700.

As shown, the optical detection system 700 may include one or more optical emitter/detector strips 702 and a control module 704. The optical emitter/detector strips 702 may include an emitter array and plurality of optical detectors of the types described herein with respect to FIGS. 1B-1C. For example, each of the illustrated emitter/detector strips 702 may include an emitter array 706 including a plurality of linearly arranged emitters, and a plurality of detectors 708 arranged linearly with respect to each other. The emitter/detector strip 702 may include a flexible substrate 703 supporting the emitter array 706 and detector 708. The use of a flexible substrate may facilitate employing the emitter/detector strip 702 in a shirt 710 or other garment. In some embodiments, the emitters and/or detectors may be embedded in the garment, such as in a fitted athletic shirt.

The control module 704 may control operation of the emitter/detector strips 702 and the processing of signals produced by the optical detectors of the emitter/detector strips 702. For example, the control module 704 may include the circuitry components shown in FIG. 3A other than the emitters and detectors. The control module may be housed in any suitable housing. In some embodiments, the control module 704 is coupled to the user, for example being affixed to the garment, held in a pocket of the garment, or otherwise held. The control module 704 may be coupled to the one or more emitter/detector strips 702 by suitable wires 712 and/or by a wireless connection. If the control module 704 and emitter/detector strips 702 are coupled wirelessly then each may include suitable wireless communication circuitry.

It should be appreciated from the foregoing description of FIG. 7 that some embodiments of the present application provide a distributed optical device. The distributed optical device may include multiple emitter and/or detector modules separated from and movable relative to a control module.

Optical systems such as system 700 of FIG. 7 may find use in a variety of settings. In some embodiments, the optical system 700 may be used to assess any of the physical quantities described herein for the purpose of providing input to a user on physical activity, including short term physical activity such as strength training. The optical emitters and detectors may be positioned to monitor specific muscle groups, such as biceps or the abdomen.

Aspects of the present application relate to apparatus and methods for providing input to a user as to how to alter user activity in light of determined oxygenation levels. As has been described, apparatus and methods are provided for determining any one or more of $SmO_2$, Hb, $HbO_2$, or HbT. This information may be valuable to a user, such as an athlete, in terms of assessing physical performance. According to an aspect of the present application, feedback is provided to the user in the form of an assessment, for example via a dashboard-type interface, and/or a recommendation. For example, a user may be notified about how the $SmO_2$, Hb, and/or $HbO_2$ compares to a target threshold. As an example, depending on whether $SmO_2$, Hb, $HbO_2$, or HbT is increasing, plateauing, or decreasing, and the magnitude of any changes, a recommendation may be provided to the user as to whether the use should increase or decrease physical activity.

The feedback may be provided to the user via smartphone, tablet, computer, sports watch, or other suitable device, and may be provided continuously, in real time, periodically, or subsequent to activity. For example, FIGS. 8A-8E illustrate examples of feedback which may be provided, with oxygenation percentage shown on the y-axes and time on the x-axes. Specifically, in the non-limiting examples of FIGS. 8A-8C, an interface 800 displayed on a phone 801 may include a time block 802 indicating a time duration of physical activity, a distance indicator 804 providing an indication of distance traveled during the activity, a chart 806 illustrating oxygenation percentage during the physical activity, an assessment block 808 providing an assessment of the physical state of the user, and a sliding graph 810 providing a sliding indication of the oxygenation percentage.

Figure 8A:
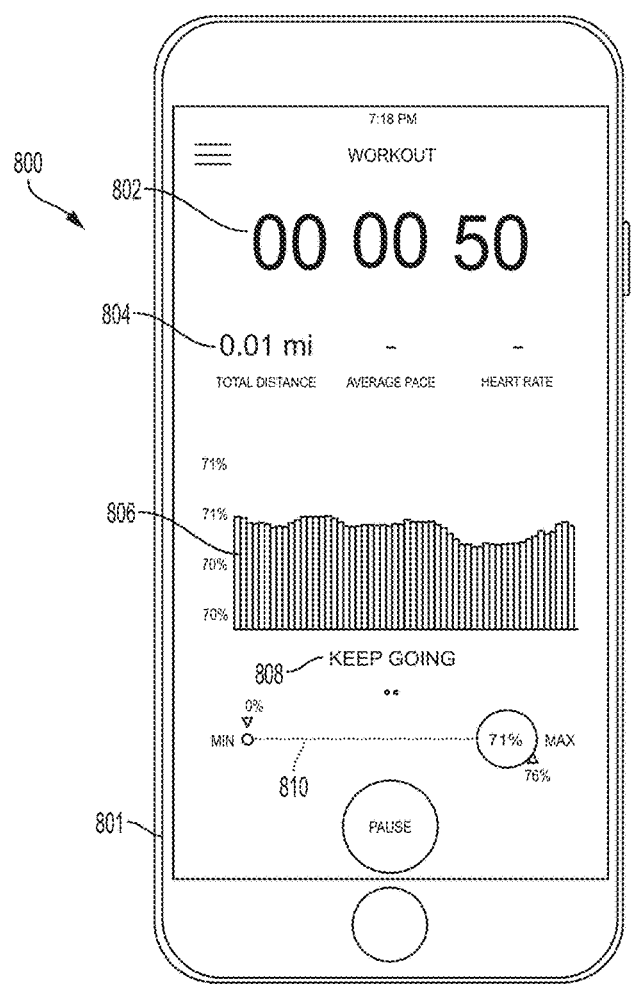
FIGS. 8A-8E illustrate examples of a dashboard as may be implemented on a processing device to provide input to a user on physical activity.
Figure 8B:
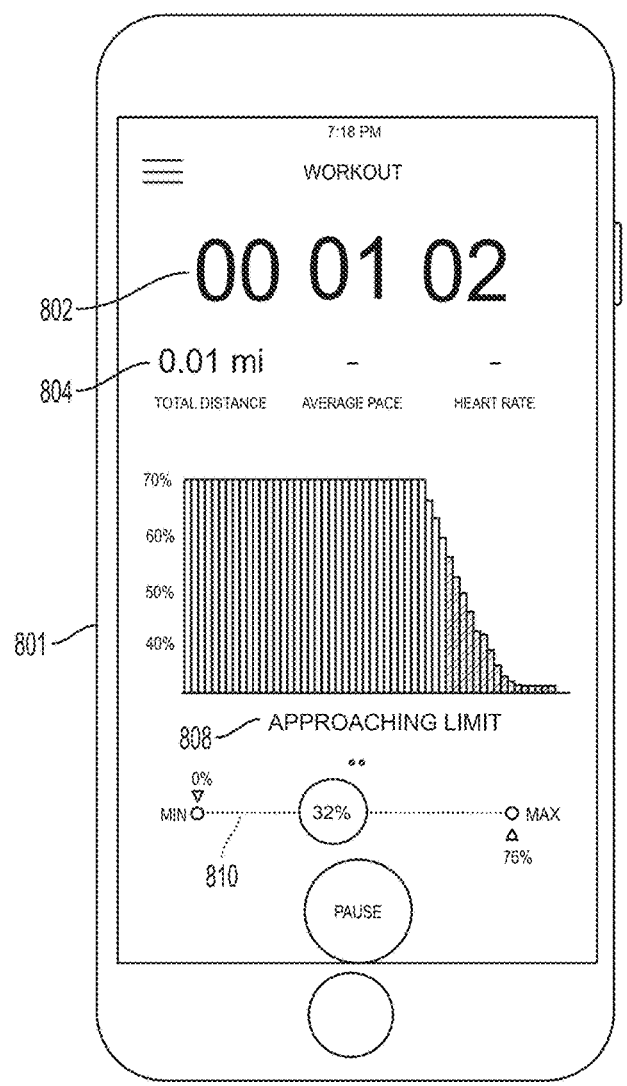
Figure 8C:
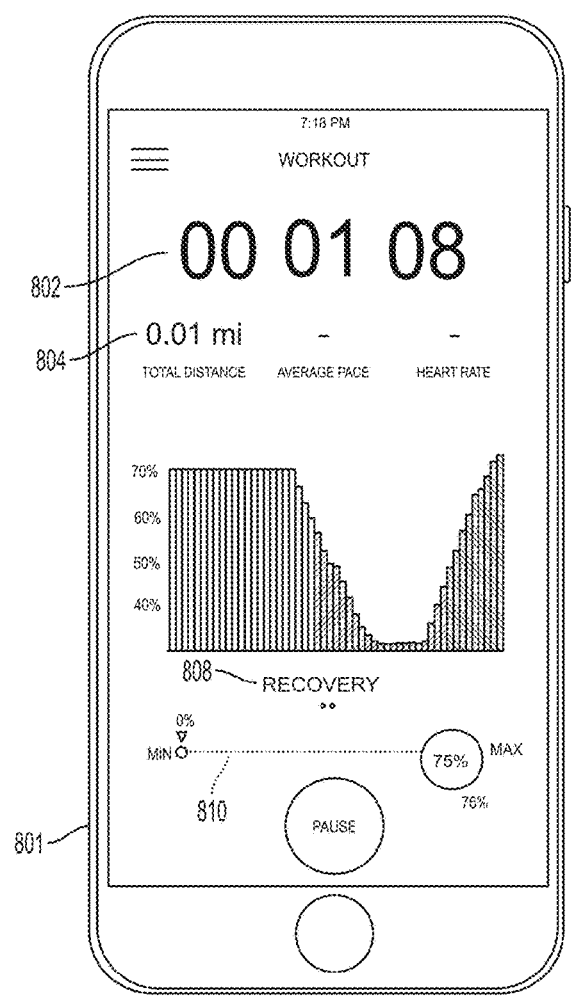
Figure 8D:
Figure 8E:
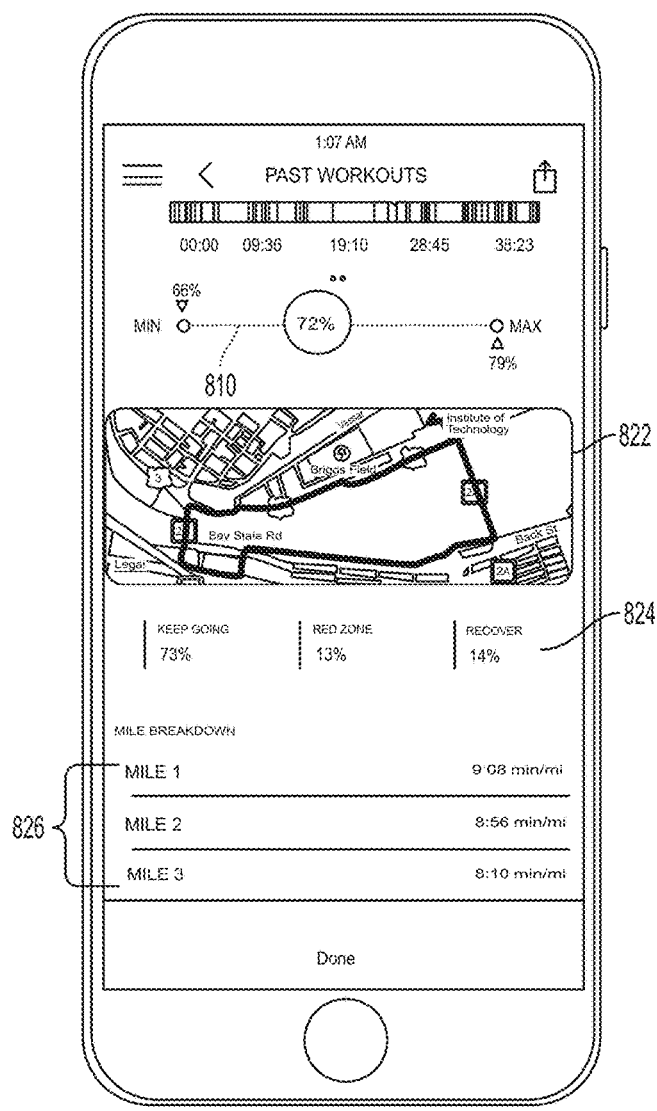

FIG. 8D illustrates a graphical user interface 820 which displays in its bottom portion a map 822 of a path taken by the user. FIG. 8E expands on the bottom portion of FIG. 8D by additionally displaying the percentage of time 824 the user spends in each state, and the time splits 826. That is, FIG. 8E is the bottom portion of the screen shown in FIG. 8D. These two images show an example of a summary that can be provided to a user upon completion of an activity. This summary can provide various information about the activity, such as classifying the activity as more of an "endurance" or "interval" activity, quantifying the user's measured level of effort, for instance by displaying the percentage of time of the activity that was spent in a given state, and many other metrics derived from the activity itself, as well as comparing the activity to past activities. For instance, if the user's performance appears to be increasing, decreasing, or remaining constant with each consecutive activity. The information may optionally be used to generate a recommendation to the user, as to how future activities could be tailored to achieved improved results.

While aspects of the present application have been described in the context of monitoring muscle oxygenation, other aspects may be used to assess muscle metabolism or performance more generally. Using Hb, $HbO_2$, and HbT to assess performance level can also be done. In addition, the magnitude and trends of these optically measured parameters can be analyzed over given time windows. The time window selected may provide important information in regards to the muscle hemodynamics, which may be indicative of performance. Beyond just Hb, $HbO_2$, HbT, and $SmO_2$, other parameters may be used to quantify an athlete's workout. For example cadence could be monitored from the optical signals sensitive to motion, or an accelerometer within the sensor. Other parameters may be measured using other peripherals that can communicate with the sensor, for example, external heart rate monitors, or GPS devices. The variety of parameters recorded could be used to evaluate athletic performance. Having more information about the user during activity can help provide a more complete picture, allowing for more accurate feedback. For instance, with GPS data during an outdoor activity, the hemoglobin parameters may be examined with GPS track and speed data, to better understand if the user has more trouble running uphill, or downhill, and how future training could be tailored to address these deficiencies. Also, limitations in certain physiological systems may be identified by, for example, monitoring heart rate and comparing this to hemoglobin parameters, to again inform training recommendations.

Also, while the users of the technology may be humans in some embodiments, in other embodiments the aspects described herein may be used to assess muscle performance of animals, such as horses.

Aspects of the present application provide a charger for charging an optical device of the types described herein. An example is described in connection with FIGS. 9A-9B.

Figure 9A:
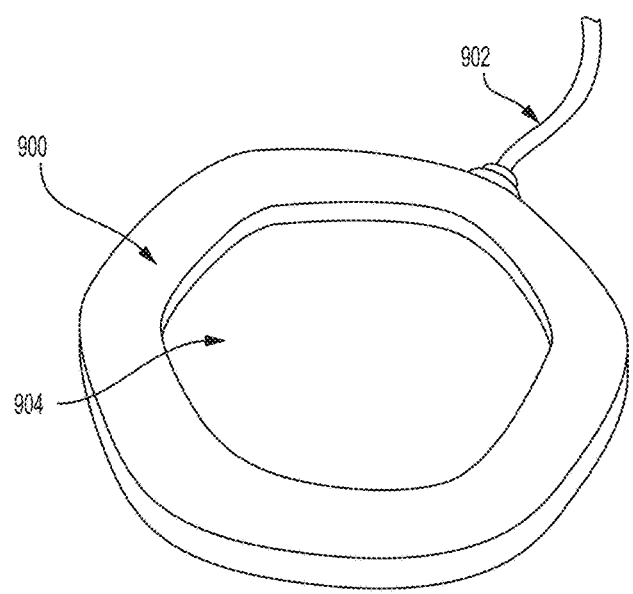
FIG. 9A illustrates a wireless charger for charging optical devices of the types described herein.

As shown in FIG. 9A, a charger 900 may be provided. The charger 900 may be couplable to a power source via a wire or cable 902. The charger 900 may include suitable circuitry for charging an optical device, such as pins, coils, ports, or other components. In some embodiments, the charger 900 is configured to wirelessly charge an optical device of the types described herein, and therefore may include charging coils configured to transmit a suitable charging signal (or power signal) to the optical device.

Figure 9B:
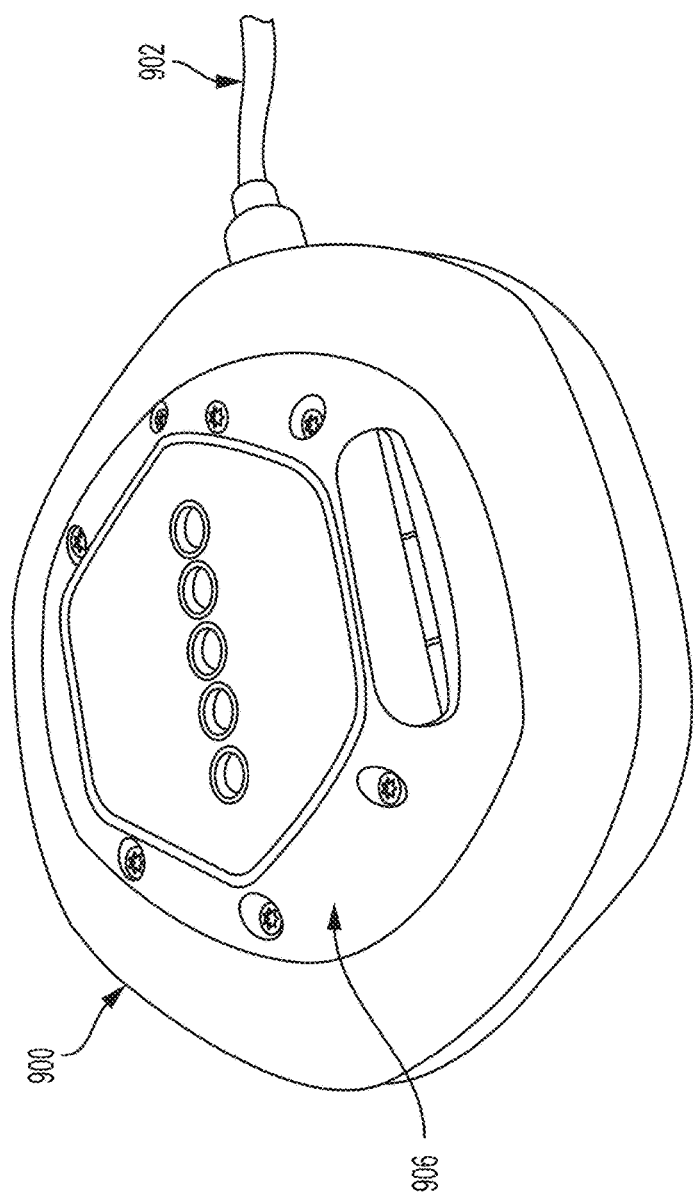
FIG. 9B illustrates an optical device coupled to the charger of FIG. 9A.

The charger 900 may have any suitable shape to mate with or otherwise charge the optical device. For example, as shown in FIG. 9A, the charger 900 may have a depression or recess 904 shaped to match the optical device. As shown in FIG. 9B, the optical device 906 may fit into the charger 900 and the charging signal may be transmitted wirelessly to the optical device.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

One or more aspects and embodiments of the present application involving the performance of methods may utilize program instructions executable by a device (e.g., a computer, a processor, or other device) to perform, or control performance of, the methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments discussed above. The computer readable medium or media can be transportable, such that the program or programs stored thereon can be loaded onto one or more different computers or other processors to implement various ones of the aspects discussed above. In some embodiments, computer readable media may be non-transitory media.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

What is claimed is:
1. A narrow-band optical device for determining muscle oxygenation level, comprising:
 a wearable housing;
 an optical source array in the wearable housing including a plurality of narrow-band optical sources;
 a plurality of optical detectors in the wearable housing including at least three optical detectors arranged substantially in a linear arrangement on a same side of the optical source array, wherein the at least three optical detectors include a first optical detector of a first size disposed a first distance from the optical source array, a second optical detector of a second size larger than the first size disposed a second distance greater than the first distance from the optical source array, and a third optical detector disposed a third distance greater than the second distance from the optical source array,
 wherein the first optical detector, the second optical detector, and the third optical detector are configured to detect an optical signal emitted from the optical source array; and a processor coupled to outputs of the plurality of optical detectors and configured to process output signals from the plurality of optical detectors and determine the muscle oxygenation level.

2. The narrow band optical device of claim 1, wherein the plurality of narrow band optical sources are arranged substantially in a linear arrangement with respect to each other, and wherein the linear arrangement of the plurality of optical sources is substantially perpendicular to the linear arrangement of the at least three optical detectors.

3. The narrow band optical device of claim 1, wherein the plurality of narrow band optical sources occupy a single position within the wearable housing.

4. The narrow band optical device of claim 1, wherein the third optical detector is larger than the second optical detector.

5. The narrow band optical device of claim 1, wherein the wearable housing includes a raised ring forming a perimeter surrounding the optical source array and the plurality of optical detectors.

6. The narrow band optical device of claim 1, further comprising a coil disposed on or within the optical housing and configured to receive wireless charging signals.

7. The narrow band optical device of claim 1, wherein the wearable housing includes a recess in which the optical source array is disposed such that the optical source array lies beneath a surface of the wearable housing.

8. The narrow band optical device of claim 1, wherein the wearable housing includes respective recesses in which the plurality of optical sources are disposed such that the plurality of optical sources lie beneath a surface of the wearable housing.

9. The narrow band optical device of claim 1, wherein the wearable housing includes respective recesses in which the plurality of optical detectors are disposed such that the plurality of optical detectors lie beneath a surface of the wearable housing.

10. The narrow band optical device of claim 1, further comprising an adjustable strap to which the wearable housing is affixed.

11. The narrow band optical device of claim 1, wherein the plurality of narrow band optical sources are arranged substantially in a linear arrangement with respect to each other, and wherein the linear arrangement of the plurality of narrow band optical sources is substantially perpendicular to the linear arrangement of the at least three optical detectors, and wherein the first optical detector is smaller than the third optical detector.

12. The optical device of claim 1, wherein the processor is disposed within the wearable housing.

13. The narrow band optical device of claim 12, further comprising wireless communication circuitry configured to wirelessly transmit data indicative of signals produced by the plurality of optical detectors.

14. The narrow band optical device of claim 1, wherein the third optical detector is larger than the first optical detector.

15. The narrow band optical device of claim 1, wherein the third optical detector is configured to detect an optical signal emitted only from optical sources that are disposed on the same side of the optical source array.

16. The narrow band optical device of claim 1, wherein the plurality of narrow band optical sources occupy a single position within the wearable housing and wherein the third optical detector is larger than the first optical detector.

* * * * *